United States Patent [19]

McCarthy

[11] Patent Number: 4,917,677
[45] Date of Patent: Apr. 17, 1990

[54] SURGICAL CLAMP ASSEMBLY AND METHOD

[76] Inventor: John A. McCarthy, 1800 N. Federal Hwy., #107, Pompano Beach, Fla. 33062

[21] Appl. No.: 330,264

[22] Filed: Mar. 29, 1989

[51] Int. Cl.⁴ .............................................. A61B 17/08
[52] U.S. Cl. .................................... 606/151; 294/99.2; 606/157
[58] Field of Search ............... 606/118, 131, 151, 157, 606/205, 206, 207, 208, 209, 210, 211; 433/3, 4, 159; 294/99.2

[56] References Cited

U.S. PATENT DOCUMENTS

| | | | |
|---|---|---|---|
| 233,964 | 11/1880 | Bear | 294/99.2 |
| 836,641 | 11/1906 | Elbert | 24/535 |
| 2,587,966 | 4/1952 | Cleary | 606/151 |
| 2,929,166 | 3/1960 | Sneide | 294/99.2 |
| 3,177,542 | 4/1965 | James | 24/125 |
| 3,210,816 | 10/1965 | Clemons | 24/73 |
| 3,265,338 | 8/1966 | Henderson | 248/27.8 |
| 3,809,094 | 5/1974 | Cook | 606/151 |
| 4,505,010 | 3/1985 | Arenhold | 24/456 |

FOREIGN PATENT DOCUMENTS

| | | | |
|---|---|---|---|
| 0348405 | 4/1905 | France | 294/99.2 |
| 0626707 | 9/1927 | France | 294/99.2 |
| 725663 | 4/1980 | U.S.S.R. | |
| 728850 | 5/1980 | U.S.S.R. | |
| 0019486 | of 1894 | United Kingdom | 294/99.2 |

Primary Examiner—Robert A. Hafer
Assistant Examiner—BethAnne Cicconi
Attorney, Agent, or Firm—Oltman and Flynn

[57] ABSTRACT

A clamp assembly and method for surgical skin removal including a first clamp with opposed, laterally elongated segments at one end which present aligned, laterally elongated, end edges and a pair of additional clamp elements with respective end edges that mate with the end edges of the first clamp. First, the first clamp is positioned clamping the skin between its laterally elongated segments, with its end edges defining the line along which the skin is to be cut. Next, the additional clamp elements are clamped against the skin with their end edges substantially mating with the end edges of the first clamp. After removal of the first clamp, the skin is cut along the end edges of the additional clamp elements and stitched together there.

15 Claims, 2 Drawing Sheets

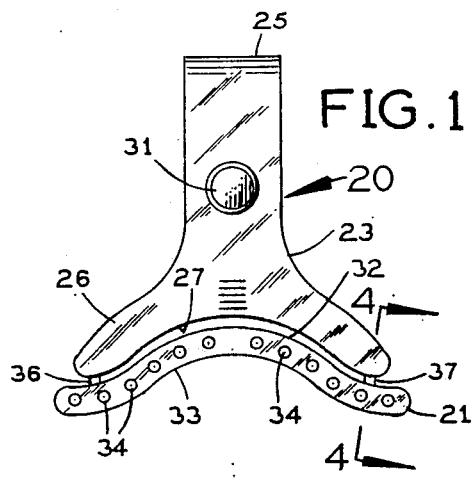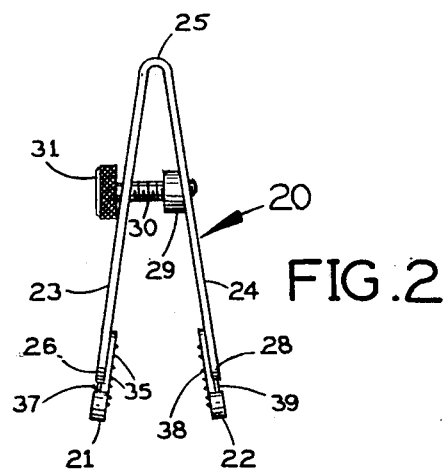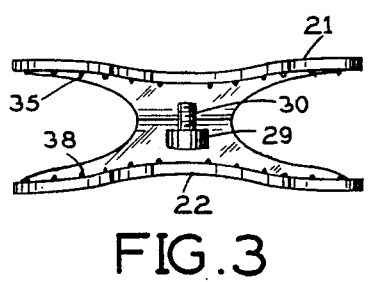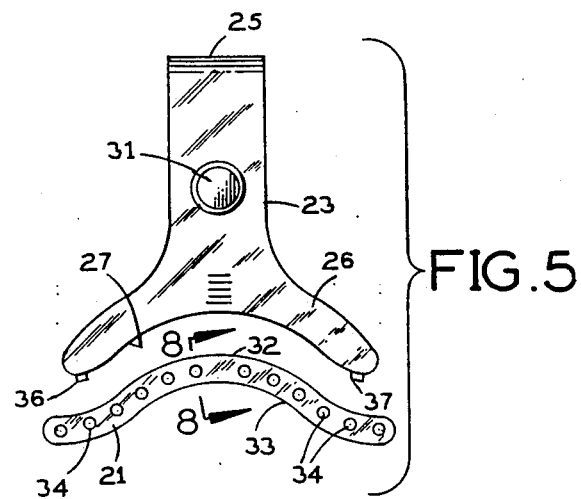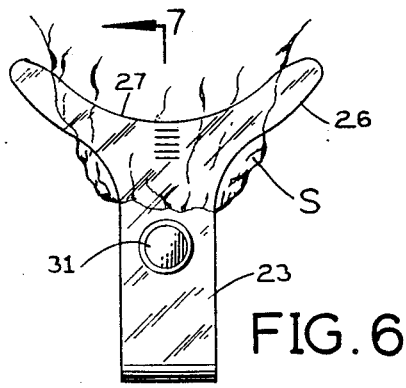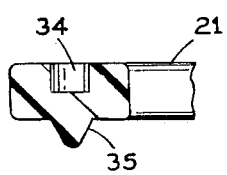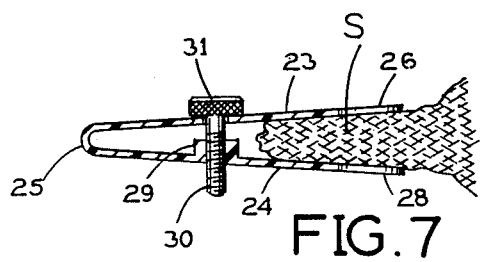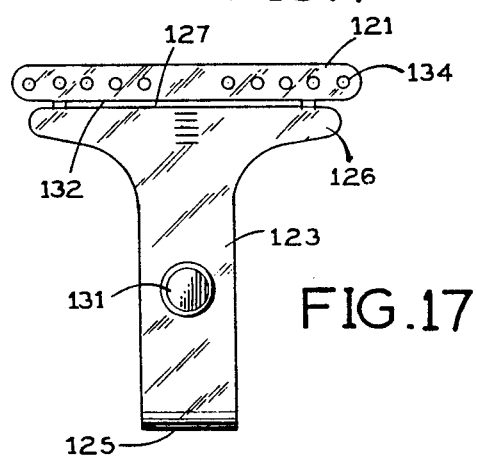

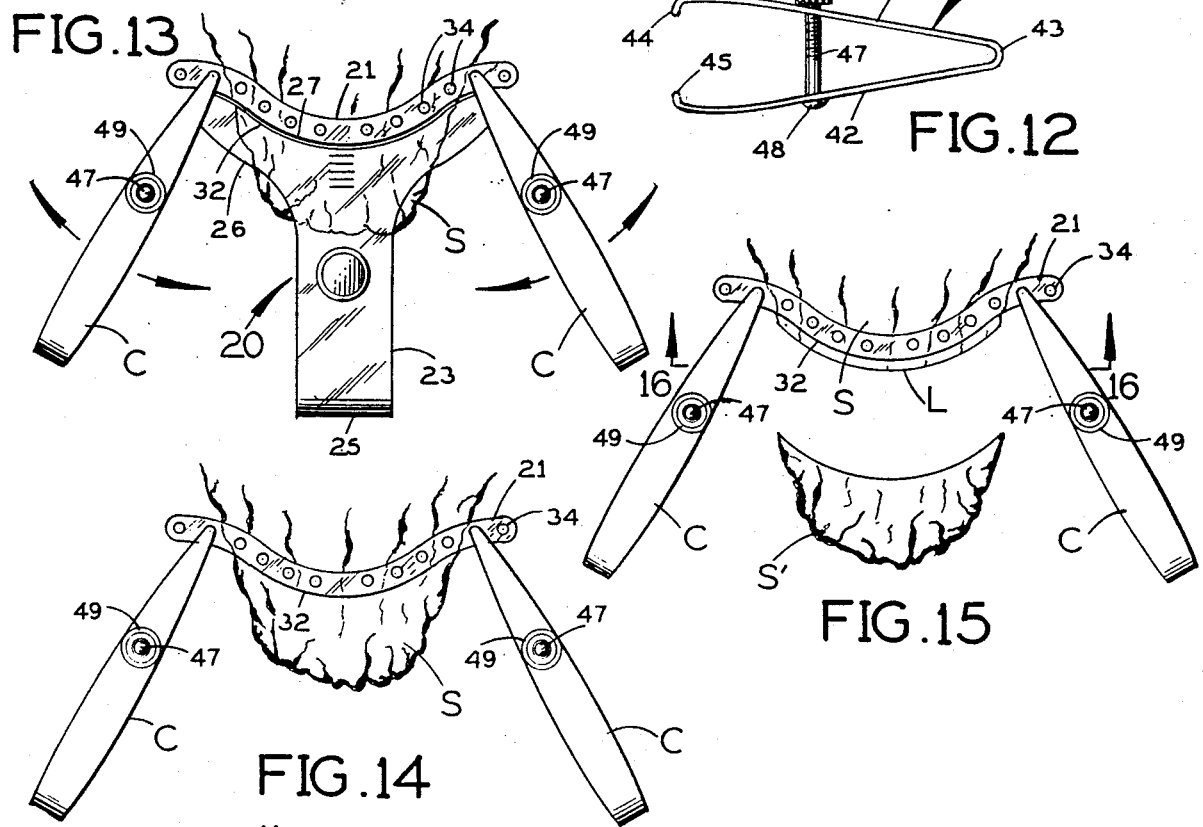

SURGICAL CLAMP ASSEMBLY AND METHOD

SUMMARY OF THE INVENTION

This invention relates to a surgical clamp assembly and to a surgical method using this clamp assembly to remove excess skin, such as from a person's eyelid.

A primary object of this invention is to provide a novel surgical clamp assembly which may be used to remove surplus skin from a person, such as at the eyelid.

Another primary object of this invention is to provide a novel method of surgically removing surplus skin.

The surgical clamp assembly in accordance with this invention has a first clamp and a pair of additional clamp elements. The first clamp has an opposed pair of arms with laterally elongated segments at one end which clamp between them the skin where surgical removal is to be performed. These laterally elongated segments of the first clamp have respective laterally elongated end edges aligned with each other. The additional clamp elements are laterally elongated and they have respective end edges that mate with the end edges of the first clamp.

First, the first clamp is clamped to a fold of skin which is to be removed surgically, with the end edges of this clamp substantially defining a line along which the skin is to be severed. Next, the additional clamp elements are positioned against the proximate segments of the skin, which are attached respectively to the skin fold that is to be removed, with their respective mating end edges in close proximity to the end edges of the first clamp. These additional clamp elements are clamped to these proximate segments of the skin. Then, the first clamp is removed, leaving the fold of skin exposed, and the surgeon severs the skin along the cut line while the additional clamp elements remain clamped against the proximate segments of the skin. Finally, the proximate segments of the skin are stitched together close to these edges of the additional clamp elements, which are removed after the stitching is completed.

Further objects and advantages of this invention will be apparent from the following detailed descriptions of two presently preferred embodiments which are illustrated schematically in the accompanying drawings.

DESCRIPTION OF THE DRAWINGS

FIG. 1 is a plan view of a unitary clamp assembly for eyelid surgery in accordance with the present invention;

FIG. 2 is a side elevation of the FIG. 1 clamp assembly;

FIG. 3 is an end elevation taken from the open end of this clamp assembly;

FIG. 4 is a fragmentary longitudinal section taken along the line 4—4 in FIG. 1;

FIG. 5 is a view similar to FIG. 1 but showing the clamp assembly after its additional clamp elements have been detached from its first clamp;

FIG. 6 is a plan view showing a fold of skin at an eyelid clamped by the first clamp of the present clamp assembly;

FIG. 7 is a longitudinal section taken along the line 7—7 in FIG. 6;

FIG. 8 is a fragmentary section taken along the line 8—8 in FIG. 5 through one of the additional clamp elements of the present clamp assembly;

FIG. 9 is a view like FIG. 6 showing the two additional clamp elements applied to segments of the skin immediately adjoining the fold of skin held by the first clamp;

FIG. 10 is a side elevation taken from the right side of FIG. 9;

FIG. 11 is a plan view of one of two identical clamps for engaging the additional clamp elements in the present invention;

FIG. 12 is a side elevation of one of these clamps;

FIG. 13 is a view like FIG. 9 showing the additional clamp elements held clamped to the skin along with the first clamp of the present clamp assembly;

FIG. 14 is a view like FIG. 13 after the removal of the first clamp, leaving the fold of skin exposed and leaving the additional clamp elements clamped to the proximate segments of the skin;

FIG. 15 is a view like FIG. 14 and showing how a fold of skin is severed, using the additional clamp elements as a guide;

FIG. 16 is an elevation showing the proximate segments of the skin stitched together along the cut line and still clamped between the additional clamp elements of the present clamp assembly; and FIG. 17 is a plan view of a second embodiment of the present clamp assembly.

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

DETAILED DESCRIPTION

Referring to FIGS. 1 and 2, the clamp assembly comprises a first clamp 20 and first and second additional clamp elements 21 and 22 detachably joined to the first clamp.

The first clamp 20 has a one-piece molded plastic body with opposed flat arms 23 and 24 (FIG. 2) interconnected at one end by a yieldable, resilient, generally U-shaped, bight segment 25. As shown in FIG. 1, at the opposite end of the first clamp from its bight segment 25 the clamp arm 23 has a laterally elongated segment 26 which extends on opposite sides of the main part of this arm. Segment 26 terminates in an exposed end edge 27 which is concave except in the vicinity of the lateral extremities of segment 26. If desired, a scale calibrated in millimeters may be provided on segment 26 of clamp arm 23 close to its end edge 27. The other arm 24 of the first clamp has an identical laterally elongated segment 28 (FIG. 2) on its end away from the bight segment 25. Segment 28 terminates in an exposed end edge (not shown) which is identical to and aligned with the end edge 27 of clamp arm 23.

On the inside, clamp arm 24 has an integral boss 29 (FIG. 2) which threadedly receives a screw-threaded bolt 30, which passes loosely through an opening in clamp arm 23 and carries an enlarged knurled head 31 engaging the outside of clamp arm 23. By grasping and turning this knob, a person may turn the bolt 30 to adjust the clamp arms 23 and 24 toward each other and bring their laterally elongated end segments 26 and 28 together to clamp skin tissue between them.

As shown in FIG. 1, the additional clamp element 21 extends parallel to the end edge 27 of arm 23 of the first clamp 20 for the entire lateral extent of edge 27 and a short distance past it on either side. Clamp element 21 present an inner end edge 32 which substantially mates with the end edge 27. The outer end edge 33 of clamp element 21 extends parallel to its edge 32, and these opposite end edges are relatively close together, so the clamp element 21 is narrow lengthwise of the first clamp 20. As shown in FIG. 8, clamp element 21 is formed with a series of cylindrical blind holes or recesses 34 in the top, spaced apart in succession along the lateral extent of this clamp element, as shown in FIG. 1. On the bottom, the clamp element 21 presents a series of similarly located projections or prongs 35 of solid, substantially conical shape.

Clamp element 21 is connected to arm 23 of the first clamp 20 by a pair of short, thin, connecting segments 36 and 37 (FIGS. 1 and 4) which can be severed readily to detach clamp element 21 from the first clamp 20.

The second additional clamp element 22 is a mirror image of clamp element 21, presenting prongs or projections 38 which face toward clamp element 21 and recesses in its bottom face like the recesses 34 in the top of clamp element 21. Clamp element 22 is connected to arm 24 of the first clamp 20 by short, thin, connecting segments, one of which appears at 39 in FIG. 2.

As shown in FIG. 3, in their normal, underformed state the two additional clamp segments 21 and 22 are bowed toward each other midway along the length of each.

Preferably, the first clamp 20, the additional clamp elements 21 and 22, and the connecting segments 36,37 and 39 which join the additional clamp elements to the respective arms 23 and 24 of the first clamp are molded integral with each other. However, if desired, the additional clamp elements 21 and 22 can be formed separate from the first clamp 20, with no connecting segments 36,37 and 39 connecting them.

In the use of this clamp assembly, if molded integral with the first clamp 20, the additional clamp elements 21 and 22 are detached from it (FIG. 5) before the first clamp is applied to the skin tissue 5 (FIG. 6) on which surgery is to be performed. In the case of an eyelid, the first clamp 20 is applied as shown in FIG. 6 to make sure the eye closes before the skin is cut. As shown in FIG. 7, bolt 30 is turned to tighten this clamp. The first clamp clamps a fold of skin that is to be removed surgically. The end edge 27 of clamp arm 23 and the corresponding end edge of clamp arm 24 substantially define the lien along which the skin is to be cut, hereinafter called the "cut line".

Next, as shown in FIG. 9, the additional clamp elements 21 and 22 are placed against the proximate segments of the skin which are joined respectively to the fold of skin that is to be removed surgically. The edge 32 of clamp element 21 is positioned as close as possible to the end edge 27 of the laterally elongated end segment 26 of clamp arm 23. Likewise, the corresponding edge of clamp element 22 is positioned as close as possible to the end edge of the laterally elongated segment 28 of clamp arm 24.

Next, as shown in FIG. 13, the two additional clamp elements 21 and 22 are clamped in this position against the respective proximate segments of the skin S by a pair of clamps C as shown in FIG. 11 and 12. Each clamp C has upper and lower opposed arms 41 and 42 (FIG. 12) connected to each other at one end by a yieldable, resilient, generally U-shaped, bight segment 43 and having short lips 44 and 45 extending toward each other at the opposite end of the clamp. These lips fit in the recesses 34 in the top of clamp element 21 and in the corresponding recesses in the bottom of clamp element 22. Clamp C has a threaded bolt 47 extending loosely up through an opening in the bottom leg 42 and having an enlarged head 48 engaging beneath this leg. Bolt 47 passes up loosely through an opening in the top leg 41 of clamp C. A knurled nut 49 threadedly engages bolt 47 above the top leg 41. By tightening this nut, the end lips 44 and 45 on the clamp C can be drawn together to hold the clamp elements 21 and 22 against the skin S in FIG. 13.

As shown by the arrows in FIG. 13, clamps C may be turned back and forth to facilitate suturing.

With the additional clamp elements 21 and 22 held clamped against proximate segments of the skin, the surgeon removes the first clamp 20 from the fold of skin, leaving it exposed and leaving the additional clamp elements 21 and 22 in place (FIG. 14).

Now the surgeon cuts the skin along the cut line L a short distance from the edge 32 of clamp element 21 and the corresponding edge of clamp element 22, using these edges as a guide so that the fold S' skin is severed from the proximate segments of the skin (FIG. 15). The surgeon leaves just enough skin of these proximate segments protruding past the edge 32 of clamp element 21 and the corresponding edge of clamp element 22 to permit these proximate segments of the skin to be stitched together by sutures 50 (FIG. 16). After the skin has been stitched together, the clamp elements 21 and 22 may be removed.

It is to be understood that the present invention may be used to remove excess skin elsewhere on the body than at the eyelid, in which case the shape of the cut line may be different from what is shown in FIG. 15. For example, where the cut line will be straight, a clamp assembly as shown in FIG. 17 may be used. Elements of this clamp assembly which correspond to elements of the clamp assembly shown in FIGS. 1–16 are given the same reference numerals plus 100 as in FIGS. 1–16. The detailed description of these elements need not be repeated. The steps in using this clamp assembly are the same as the steps already described, the only difference being that the cut line will be straight instead of convex.

All clamps are preferably transparent.

I claim:

1. A surgical clamp assembly comprising:

a first clamp having a pair of opposed arms with laterally elongated segments at one end facing each other, each of said segments having an exposed laterally elongated end edge, said end edges of the arms being aligned with each other, and means for selectivley adjusting said arms of the first clamp toward each other to clamp between said laterally elongated segments a fold of skin that is to be surgically removed along a cut line located substantially along said end edges of said arms;

and a pair of additional clamp elements for clamping engagement respectively with proximate segments of the skin immediately adjoining said fold of skin in immediate proximity to said end edges of said laterally elongated segments of said arms, each of said clamp elements having a narrow dimension lengthwise of the corresponding arm and being elongated laterally of the corresponding arm, each of said clamp elements having an end edge which mates with said end edge of said laterally elongated segment on the corresponding arm, at least one of said clamp elements having projections facing the other clamp element.

2. A surgical clamp assembly according to claim 1 wherein said opposed arms of said first clamp and said additional clamp elements are integrally molded in a one-piece plastic body having severable connecting segments between said end edges of said laterally elongated segments of the arms and said end edges of said clamp elements.

3. A surgical clamp assembly according to claim 2 wherein said plastic body has a bight segment interconnecting said arms at the opposite end from said laterally elongated segments of each arm.

4. A surgical clamp assembly according to claim 3 wherein said means for selectively adjusting said arms comprises a screw-threaded bolt acting between said arms.

5. A surgical clamp assembly according to claim 4 wherein each of said additional clamp elements has a plurality of prongs spaced apart in succession laterally of said clamp element and facing the other clamp element.

6. A surgical clamp assembly according to claim 5 wherein each of said additional clamp elements has a plurality of recesses spaced apart in succession laterally of said clamp element and facing away from the other clamp element.

7. A surgical clamp assembly according to claim 3 wherein each of said additional clamp elements has a plurality of prongs spaced apart in succession laterally across said clamp element and facing the other clamp element.

8. A surgical clamp assembly according to claim 7 wherein each of said clamp elements has a plurality of recesses spaced apart in succession laterally of said clamp element on the side away from the other clamp element.

9. A surgical clamp assembly according to claim 1 wherein each of said clamp elements has a plurality of prongs spaced apart in succession laterally across said clamp element and facing the other clamp element.

10. A surgical clamp assembly according to claim 9 wherein each of said clamp elements has a plurality of recesses spaced apart in succession laterally of said clamp element on the side away from the other clamp element.

11. A surgical clamp assembly comprising:
a first clamp having a pair of opposed arms with laterally elongated segments at one end facing each other, each of said segments having an exposed laterally elongated end edge, and means for selectively adjusting said arms toward each other to bring said laterally elongated segments together to clamp tissue between them;
and a pair of additional clamp elements for clamping engagement respectively with the tissue in immediate proximity to said end edges of said laterally elongated segments of said arms, each of said clamp elements having a narrow dimension lengthwise of the corresponding arm and being elongated laterally of the corresponding arm, each of said clamp elements having an end edge which mates with said end edge of said laterally elongated segment on the corresponding arm, at least one of said clamp elements having projections facing the other clamp element.

12. A method of surgically removing skin comprising the steps of:
clamping a fold of skin that is to be surgically removed between opposed laterally elongated arms of a first clamp which have laterally elongated, exposed, end edges aligned with each other and substantially defining a line along which the skin is to be cut;
positioning against proximate segments of the skin which are joined respectively to said fold of skin a pair of additional clamp elements in immediate proximity to said end edges of the first clamp, each of said additional clamp elements having an exposed laterally elongated edge which substantially mates with the adjacent end edge of said first clamp;
clamping said additional clamp elements against said proximate segments of the skin;
removing said first clamp from said fold of skin, leaving said fold of skin exposed beyond said end edges of said additional clamp elements;
and, while said additional clamp elements remain clamped against said proximate segments of the skin, cutting the skin along said line in close proximity to said end edges of said additional clamp elements to sever said fold of skin from said proximate segments of the skin.

13. A surgical method according to claim 12 and comprising the additional step of stitching together said proximate segments of the skin close to said line along which the skin has been cut while maintaining said additional clamp elements clamped to said proximate segments of the skin.

14. A surgical method comprising the steps of:
clamping tissue between an opposed pair of laterally elongated segments of a first clamp which have respective exposed laterally elongated end edges aligned with each other on opposite sides of said tissue;
positioning in immediate proximity to said end edges of said first clamp a pair of additional clamp elements, each having an exposed laterally elongated edge which mates with the corresponding end edge of said first clamp;
clamping said additional clamp elements against said tissue;
removing said first clamp from said tissue; and, while said additional clamp elements remain clamped against said tissue, severing said tissue in close proximity to said laterally elongated edges of said additional clamp elements.

15. A surgical method according to claim 14 and comprising the additional step of stitching the remaining tissue together along said laterally elongated edges of said additional clamp elements while maintaining said additional clamp elements clamped to said remaining tissue.

* * * * *